(12) United States Patent
Haslinger et al.

(10) Patent No.: US 9,089,669 B2
(45) Date of Patent: Jul. 28, 2015

(54) APPARATUS AND METHOD OF MAKING A VARIABLE STIFFNESS MULTILAYER CATHETER TUBING

(71) Applicant: Abbott Cardiovascular Systems Inc., Santa Clara, CA (US)

(72) Inventors: Thomas F. Haslinger, Sun City, CA (US); John A. Simpson, Carlsbad, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 279 days.

(21) Appl. No.: 13/889,620

(22) Filed: May 8, 2013

(65) Prior Publication Data
US 2013/0245610 A1 Sep. 19, 2013

Related U.S. Application Data

(62) Division of application No. 12/769,865, filed on Apr. 29, 2010, now Pat. No. 8,440,090.

(51) Int. Cl.
| | |
|---|---|
| *A61M 25/00* | (2006.01) |
| *A61M 25/10* | (2013.01) |
| *B29C 65/68* | (2006.01) |
| *B29C 65/00* | (2006.01) |
| *B29C 47/00* | (2006.01) |
| *B29C 47/02* | (2006.01) |
| *B29C 47/06* | (2006.01) |
| *B29C 61/00* | (2006.01) |
| *B29L 31/00* | (2006.01) |

(52) U.S. Cl.
CPC ....... *A61M 25/0045* (2013.01); *A61M 25/0009* (2013.01); *A61M 25/0054* (2013.01); *A61M 25/10* (2013.01); *B29C 47/0023* (2013.01); *B29C 65/68* (2013.01); *B29C 66/1142* (2013.01); *B29C 66/5221* (2013.01); *B29C 66/723* (2013.01); *A61M 2025/1061* (2013.01); *B29C 47/0014* (2013.01); *B29C 47/0066* (2013.01); *B29C 47/021* (2013.01); *B29C 47/065* (2013.01); *B29C 61/006* (2013.01); *B29C 66/71* (2013.01); *B29C 2793/0036* (2013.01); *B29C 2793/0054* (2013.01); *B29C 2793/0063* (2013.01); *B29K 2995/0082* (2013.01); *B29L 2031/7542* (2013.01); *Y10T 156/1066* (2015.01)

(58) Field of Classification Search
CPC ..................... A61M 25/0045; A61M 25/0009; A61M 25/10
See application file for complete search history.

(56) References Cited

U.S. PATENT DOCUMENTS

| | | | | |
|---|---|---|---|---|
| 6,165,166 | A * | 12/2000 | Samuelson et al. | 604/524 |
| 2008/0262472 | A1 | 10/2008 | Lunn et al. | |
| 2010/0145430 | A1 | 6/2010 | Wübbeling et al. | |
| 2013/0046236 | A1 | 2/2013 | Ponzi et al. | |

\* cited by examiner

*Primary Examiner* — Nicholas Lucchesi
*Assistant Examiner* — Melissa A Snyder
(74) *Attorney, Agent, or Firm* — Fulwider Patton LLP

(57) ABSTRACT

A catheter body having a variable stiffness along its longitudinal length and a method for manufacturing same is disclosed wherein an inner layer having an uninterrupted length serves as a backbone for segments of coextrusion of, e.g., Pebax or nylon and a tie layer which are then bonded to the backbone to create a multi-stiffness catheter body.

13 Claims, 4 Drawing Sheets

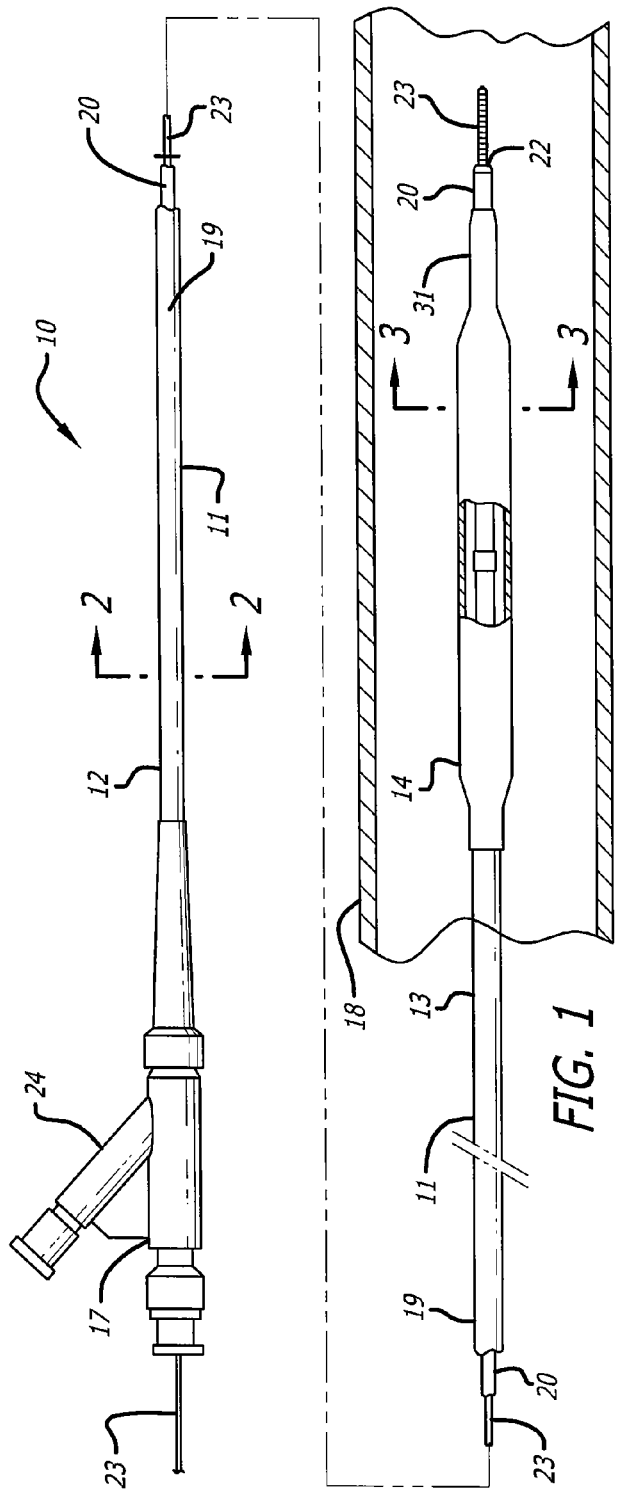

APPARATUS AND METHOD OF MAKING A VARIABLE STIFFNESS MULTILAYER CATHETER TUBING

This Preliminary Amendment is being filed concurrently with an application that is a division of U.S. Ser. No. 12/769,865 filed Apr. 29, 2010, the entirety of which is incorporated herein by reference.

BACKGROUND

This invention generally relates to catheters, and particularly to intravascular catheters for use in percutaneous transluminal coronary angioplasty (PTCA) or for the delivery of stents.

In percutaneous transluminal coronary angioplasty (PTCA) procedures, a guiding catheter is advanced in the patient's vasculature until the distal tip of the guiding catheter is seated in the ostium of a desired coronary artery. A guidewire is first advanced out of the distal end of the guiding catheter into the patient's coronary artery until the distal end of the guidewire crosses a lesion to be dilated. A dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with inflation fluid one or more times to a predetermined size at relatively high pressures so that the stenosis is compressed against the arterial wall and the wall expanded to open up the vascular passageway. Generally, the inflated diameter of the balloon is approximately the same diameter as the native diameter of the body lumen being dilated so as to complete the dilatation but not over expand the artery wall. After the balloon is finally deflated, blood resumes through the dilated artery and the dilatation catheter and the guidewire can be removed.

In such angioplasty procedures, there may be restenosis of the artery, i.e., reformation of the arterial blockage, which necessitates either another angioplasty procedure, or some other method of repairing or strengthening the dilated area. To reduce the restenosis rate of angioplasty alone and to strengthen the dilated area, physicians may implant an intravascular prosthesis, generally called a stent, inside the artery at the site of the lesion. Stents may also be used to repair vessels having an intimal flap or dissection or to generally strengthen a weakened section of a vessel or to maintain its patency.

Stents are usually delivered to a desired location within a coronary artery in a contracted condition on a balloon of a catheter which is similar in many respects to a balloon angioplasty catheter, and expanded within the patient's artery to a larger diameter by expansion of the balloon. The balloon is deflated to remove the catheter and the stent left in place within the artery at the site of the dilated lesion. For details of stents, see for example, U.S. Pat. No. 5,507,768 (Lau, et al.) and U.S. Pat. No. 5,458,615 (Klemm, et al.), which are incorporated herein by reference.

An essential step in effectively performing a PTCA procedure is properly positioning the balloon catheter at a desired location within the coronary artery. To properly position the balloon at the stenosed region, the catheter must have good pushability (i.e., ability to transmit force along the length of the catheter), and good trackability and flexibility, to be readily advanceable within the tortuous anatomy of the patient's vasculature. Conventional balloon catheters for intravascular procedures, such as angioplasty and stent delivery, frequently have a relatively stiff proximal shaft section to facilitate advancement of the catheter within the patient's body lumen and a relatively flexible distal shaft section to facilitate passage through tortuous anatomy such as distal coronary and neurological arteries without damage to the vessel wall. These flexibility transitions can be achieved by a number of methods, such as bonding two or more tubing segments of different flexibility together to form the shaft. However, such transition bonds must be sufficiently strong to withstand the pulling and pushing forces on the shaft during use. At present, however, there are distinct shortcomings associated with the methods of manufacture proposed to produce a catheter with this characteristic. In particular, current methods do not satisfy the necessary tensile strength requirements set for such devices.

One proposed method of creating a varying stiffness catheter involves cutting segments of different multi-layer tubular members and joining them together end to end, with the outermost layer of the distal segment(s) having a reduced durometer and/or thickness compared with that of its adjacent more proximal segment. While this technique was used to produce samples which were bench tested to prove the merit of the technology with regard to deliverability, the joints created by the mating of the segments were not sufficiently robust to meet product tensile strength and other reliability requirements. The reason for this is that most catheter tubings are multi-layers, such as tri-layer extrusions. These three-layer configurations have an innermost layer that is particularly difficult to join end-to-end, because the innermost layer is typically constructed of high density polyethylene (HDPE), which is not melt-bond compatible with a nylon or Pebax outermost layer. Attempts to either butt-join or lap-join tri-layer inner member segments have been unsuccessful because all abutting or overlapping layers did not bond reliably to one another.

Past approaches to improve joint reliability and overall manufacturability have all suffered several common drawbacks: the tubing needed to be heated along its entire length to bond the various pieces together; and an entire length of shrink tubing covering the length of the tubing must be used to bond the layers and then discarded. For rapid exchange balloon catheters and other catheters, where the variable stiffness tubing spans approximately 25 cm within the finished device, the extended shrink tubing amounts to a considerable overall cost increase (multiple extrusions, shrink tubing, more direct labor required for assembly) relative to a conventional tri-layer extrusion. For over the wire balloon catheters, in which the variable stiffness tubing can be approximately five times longer, the cost becomes essentially prohibitive.

SUMMARY OF THE INVENTION

This present invention is an apparatus and method for producing a multi-layer catheter tubing whose outermost layer is comprised of polymers of different stiffness along its length and the innermost layer is an uninterrupted lubricious layer. This invention enables the assembly of various outer layer segments, including tungsten-filled polymer segments serving as balloon markers, onto the uninterrupted innermost layer without having to process the entire length of the tubing with progressive heating and shrink tubing. Rather, only short distal regions require heat and shrink tubing. This is particularly significant for over the wire catheters.

BRIEF DESCRIPTION OF THE DRAWINGS

FIG. 1 is an elevated, perspective view, partially in cutaway, of a catheter of the kind constructed by the present invention;

FIG. 2 is a cross-sectional view of the catheter of FIG. 1 taken along lines 2-2;

FIG. 3 is a cross-sectional view of the catheter of FIG. 1 taken along lines 3-3;

DETAILED DESCRIPTION OF THE PREFERRED EMBODIMENTS

Figure 4:
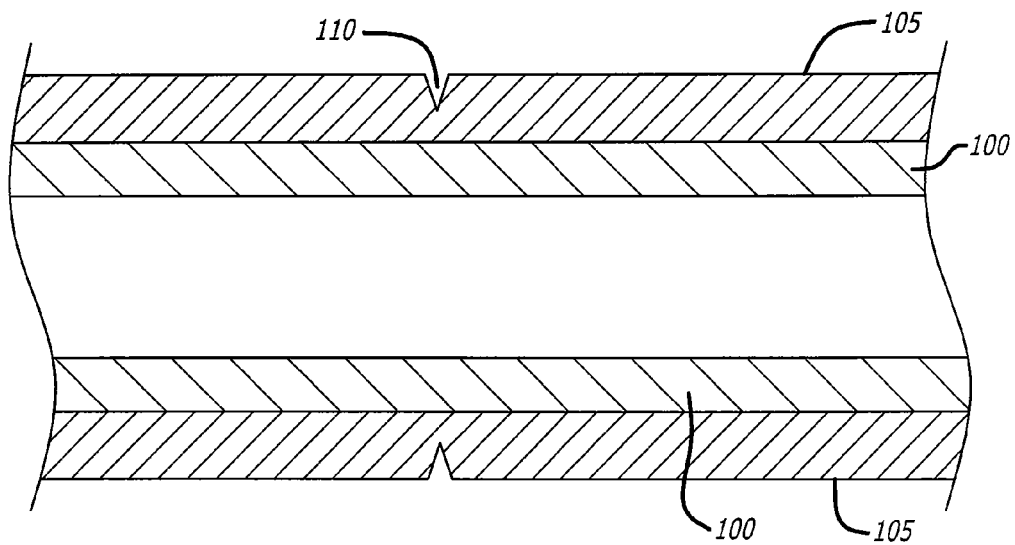
FIG. 4 is an enlarged, cross-sectional view of a portion of the body of the tubing used to construct the catheter of FIG. 1.

FIG. 1 illustrates a balloon catheter of the type that can benefit from the present invention. The catheter 10 of the invention generally comprises an elongated catheter shaft 11 having a proximal section, 12 a distal section 13, an inflatable balloon 14 formed of a blend of polymeric materials on the distal section 13 of the catheter shaft 11, and an adapter 17 mounted on the proximal section 12 of shaft 11. In FIG. 1, the distal portion of the catheter 10 is illustrated within a patient's body lumen 18, prior to expansion of the balloon 14.

In the embodiment illustrated in FIG. 1, the catheter shaft 11 has an outer tubular member 19 and an inner tubular member 20 disposed within the outer tubular member defining, with the outer tubular member, an inflation lumen 21. Inflation lumen 21 is in fluid communication with the interior chamber 15 of the inflatable balloon 14. The inner tubular member 20 has an inner lumen 22 extending therein which is configured to slidably receive a guidewire 23 suitable for advancement through a patient's coronary arteries. The distal extremity 31 of the inflatable balloon 14 is sealingly secured to the distal extremity of the inner tubular member 20 and the proximal extremity 32 of the balloon 14 is sealingly secured to the distal extremity 13 of the outer tubular member 19.

FIGS. 2 and 3 show transverse cross sections of the catheter shaft 11 and balloon 14, respectively, illustrating the guidewire receiving lumen 22 of the guidewire's inner tubular member 20 and inflation lumen 21 leading to the balloon interior 15. The balloon 14 can be inflated by radiopaque fluid introduced at the port in the side arm 24 into inflation lumen 21 contained in the catheter shaft 11, or by other means, such as from a passageway formed between the outside of the catheter shaft 11 and the member forming the balloon, depending on the particular design of the catheter. The details and mechanics of balloon inflation vary according to the specific design of the catheter, and are well known in the art.

FIGS. 4-10 illustrate the various steps of constructing the variable stiffness catheter of the present invention. According to the present invention, a catheter body is formed as a dual-layer hollow extrusion with a lubricious inner layer 100 of HDPE or ultra high molecular weight polyethylene (UHMWPE) and an outer layer 105 of nylon or Pebax, omitting the usual Primacor "tie layer" that binds the inner layer 100 to the outer layer 105. This extrusion serves as the "backbone" for the final inner member's entire length. As explained below, other dual-layer hollow extrusions having an inner layer of Primacor and an outer layer of nylon or Pebax will be added to provide varying bending stiffness to the distal end. Further, a tungsten-filled polymer (nylon or Pebax) hollow extrusion, with or without an inner layer of Primacor, may be utilized to provide radio-opacity at discrete locations to serve as visual markers.

Assembly begins with the following steps to remove a distal section of the "backbone" extrusion's outer Pebax or nylon layer:

Step 1: At an appropriate distance from the distal end, the outer layer of the HDPE/nylon or HDPE/Pebax "backbone" extrusion is circumferentially scored 110 using a cutting instrument such as a razor blade or the like to create a break point of the outer layer 105 only (FIG. 4). Care is called for to control the scoring blade in order to protect the inner layer 100.

Figure 5:
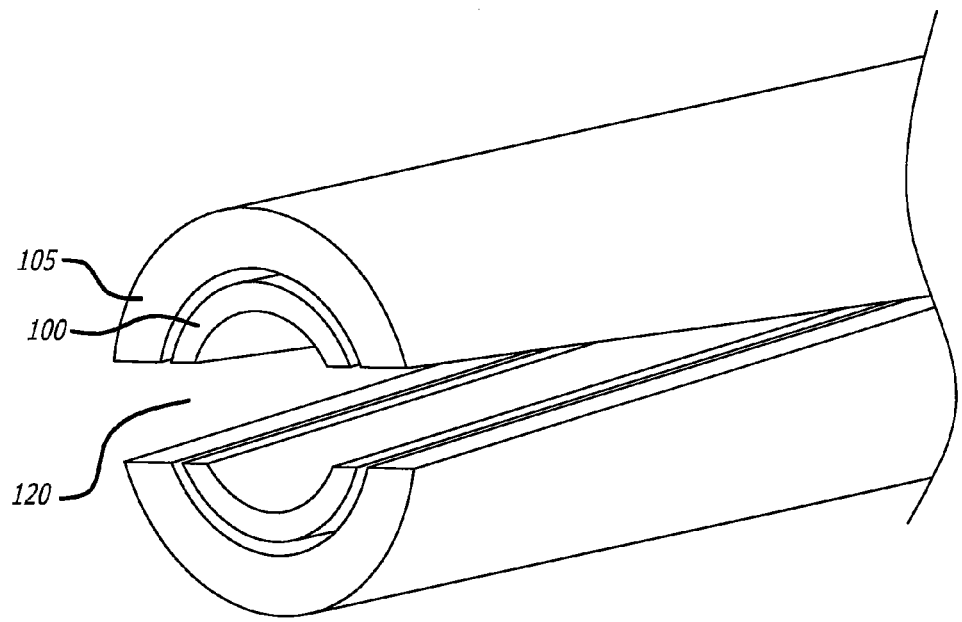
FIG. 5 is an enlarged, perspective view of the distal end of the tubing of FIG. 4.

Step 2: A longitudinal slit 120 is made at the distal end of the extrusion so as to bisect the tubing over a length of several mm or more using a cutting knife such as a razor blade or equivalent, creating two semi-circular halves at the distal end (FIG. 5).

Figure 6:
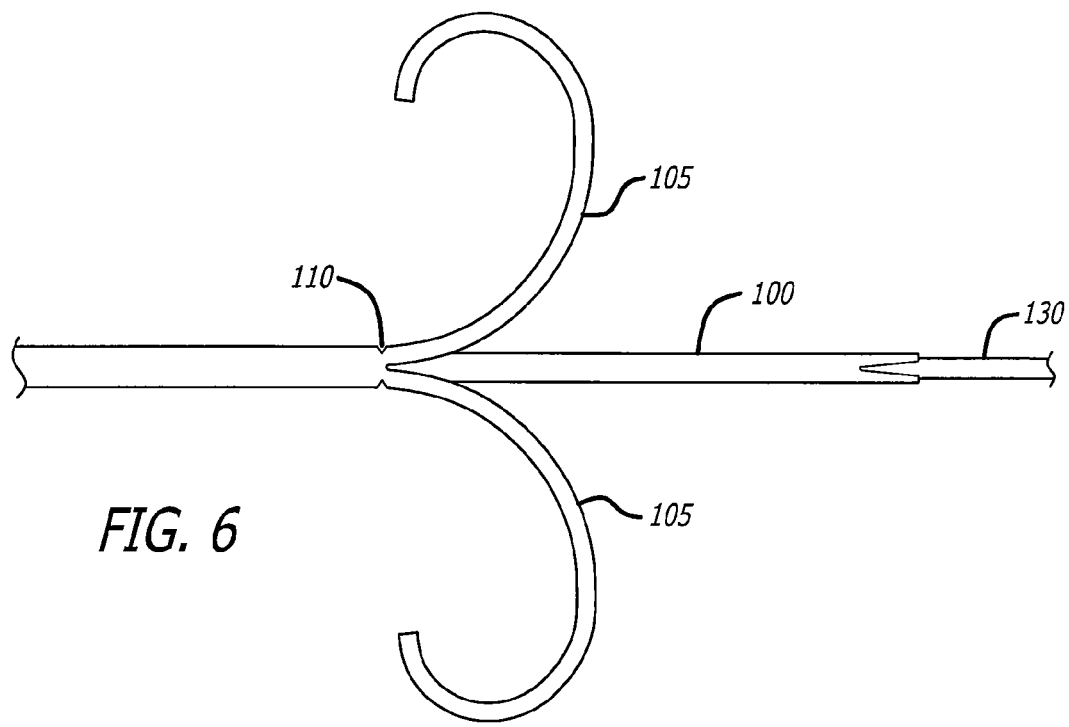
FIG. 6 is a perspective view of the distal end of the tubing as the outer layer is peeled off.

Step 3: To separate the outer layer 105 from the inner layer 100, both halves of the bisected end are folded back, and a grasping tool such as tweezers or the like is used to grasp the outer layer 105 and pull it away from the inner layer 100 of each half. The outer layer 105 of each half is then peeled away from their respective inner layer to thus separate and remove the outer layer until the score mark 110 is reached, whereupon the outer layer halves 105 tear away from the "backbone" extrusion. The result is a stepped transition 140 between the exposed HDPE inner layer 100 and the intact proximal remainder of the extrusion's outer layer 105 (FIGS. 6,7).

Although other techniques may be used to achieve the same objective, the steps above describe a simply way to remove a defined length of the top layer. Note that this objective would be difficult if not impossible to achieve if the "backbone" was a conventional tri-layer extrusion, due to the tenacious adhesive bond provided by the Primacor middle "tie-layer," and attempts to do so using the steps above have proven unsuccessful.

Figure 7:
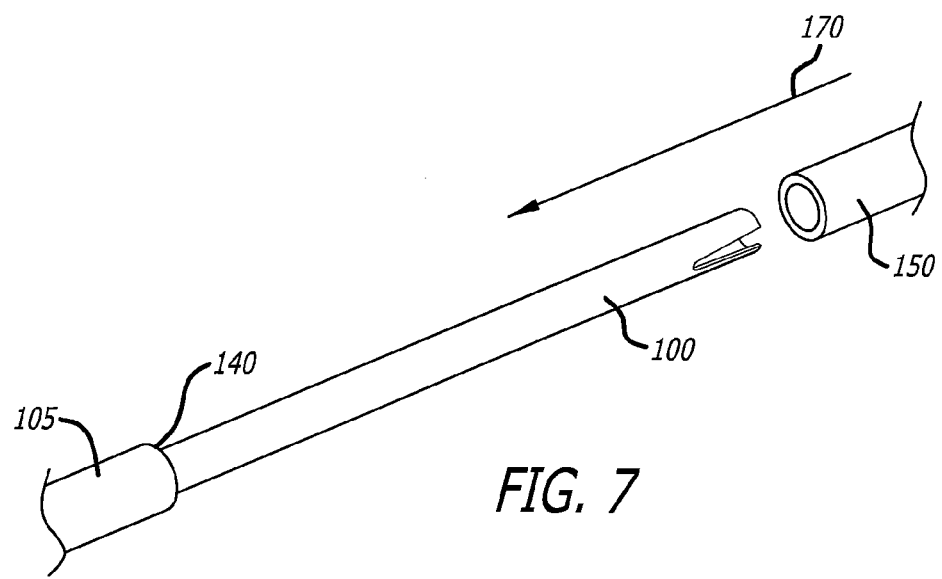
FIG. 7 is an enlarged, perspective view of a new tubing segment placed over the tubing of FIG. 6.
Figure 8:
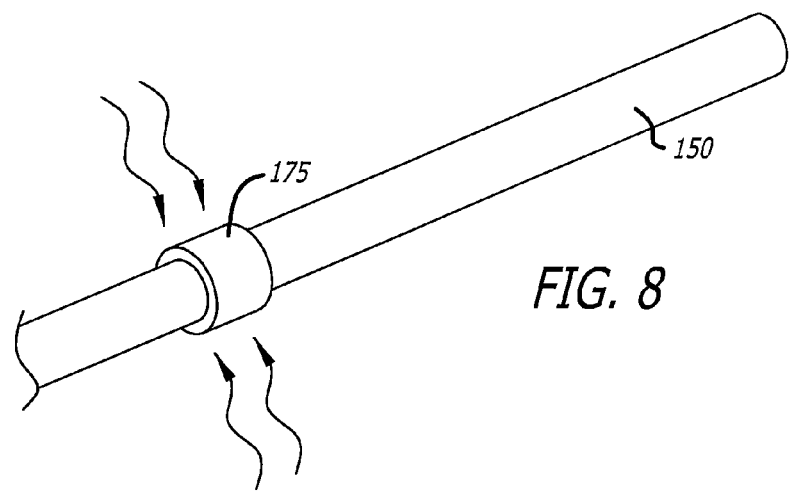
FIG. 8 is an enlarged, perspective view of the new tubing segment of FIG. 7 with shrink tubing placed over it.

Next, segments 150 of appropriate length are cut from Primacor-lined nylon and/or Pebax extrusions, and optionally segments of a tungsten-filled polymer extrusion (with or without a Primacor lining) when a visual marker is desired, and the segments 150 are slid over the exposed HDPE inner layer 100 of the "backbone" extrusion (see arrow 170 of FIG. 7). All segments 150 are butted together and a suitable length of shrink tubing 175 is placed over the region (See FIG. 8). A fluoropolymer shrink tube material, such as FEP, is preferable due to the non-stick nature. This region only is then progressively heated to melt bond the various segments 150 together and allow the Primacor to adhere or "tie" the segments to the underlying HDPE layer. Afterwards, the shrink tubing 175 and mandrel 130 are removed to leave the finished catheter body.

Figure 9:
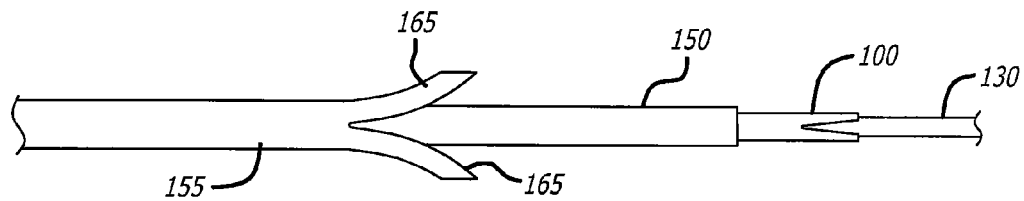
FIG. 9 is an enlarged, side view of flaps in a proximal layer being overlaid over the new tubing segment of FIG. 7.
Figure 10:
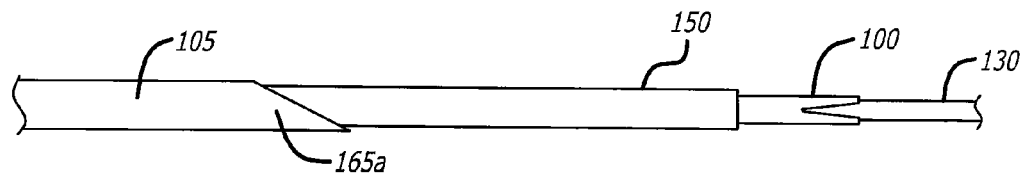
FIG. 10 is an enlarged, side view of the proximal inner member with overlapping flaps cut at an angle.

The resultant composite tubing is a variable-durometer inner member, with or without integral tungsten-filled balloon markers, whose inner HDPE layer is uninterrupted. The distal end is effectively a tri-layer and can be processed like any conventional tri-layer inner member with regard to balloon sealing, tip attachment, marker band swaging or fusing (if needed), etc. To make the transition from one durometer section to another less abrupt, the outer layer 155 of the proximal dual-layer extrusion may be left unscored prior to peeling, so the peeled strips can be trimmed with flaps 165 remaining. As illustrated in FIG. 9, these flaps can be made to overlap the adjacent segment 150 before heating with shrink tubing, so the overlapped region is comprised of both, albeit thinned, outer layers. The flaps 165a may be angle-cut to "feather" the stiffness transition, as shown in FIG. 10. Alternatively, the flaps may be purposely trimmed to differing lengths in order to further broaden the transition region.

In yet another embodiment, the proximal dual-layer extrusion is trimmed as shown in FIG. 7 and the adjacent segment is slit and made to overlap the remaining outer layer on the dual-layer extrusion before heating with the shrink tubing.

In all instances the proximal end is a dual-layer extrusion whose layers are mechanically bonded by virtue of their intimate proximity and the inherent surface roughness at their interface. The resulting variable-durometer inner member may be hot die necked, including the dual-layer proximal section, using the same methods as for conventional tri-layer extrusions. Although adding cost, hot die necking could be used to provide additional changes in stiffness, improved control of final dimensions, or increased tensile load carrying capability to the inner member. At equal final dimensions, a hot die necked inner member will typically have a greater tensile break load then one that has not been necked.

The "backbone" extrusion's outer layer 105 can be any durometer polymer, as required by the application, and its inner layer 100 can be any extrudable lubricious material. However, preferably the layer materials should not adhere well to each other during extrusion, because peeling off the outer layer 105 at the distal end would be more difficult.

The "backbone" extrusion may be E-beam irradiated, particularly if its inner layer is HDPE (or UHMWPE), as this promotes cross-linking and thus prevents undesirable material flow of the inner layer during subsequent melt bonding operations.

The added outer layer segments 150 can be any durometer polymer, as the application requires, but it is preferred that they contain an inner layer of a "tie layer" material like Primacor in order to promote secure bonding to the "backbone" extrusion's inner layer 100. The heat needed for such bonding is preferably achieved by equipment that provides localized and controllable heat with the ability to traverse or rotate, and the required radial pressure is preferably provided by shrink tubing which does not adhere well to the underlying materials. Although it would be possible to simply heat the assembly in an oven, this is less desirable because of a greater tendency to trap air beneath the shrink tubing 175 leading to surface irregularities.

This invention is also applicable to inner members whose inner layer 100 is a fluoropolymer such as PTFE. In one alternate embodiment, the inner layer 100 is a single-layer extrusion that is subsequently etched (e.g., sodium naphthalene or "Tetra Etch") to promote bondability of its outer surface. An outer layer 105 is then extruded onto the fluoropolymer tubing in a semi-continuous (reel to reel) manner, with the extrusion parameters selected to prevent melt bonding of the two layers. Thus, the outer layer 105 can be subsequently peeled away at one end to make room for the installation of various durometers of outer jacket segments 150 and tungsten-filled polymer markers. In this embodiment, the added segments 150 do not require an inner "tie layer" because they can be melt bonded directly to the etched fluoropolymer surface, again using heat and shrink tubing.

What is claimed:

1. A variable stiffness catheter tubing, comprising:
   a multi-layer extrusion having an outer layer and an inner layer, a portion of the outer layer peeled away from the inner layer at a first end;
   a first extrusion segment placed over the inner layer at the first end where the outer layer has been peeled away and joined to the outer layer of the multi-layer extrusion, where the inner layer of the multi-layer extrusion is uninterrupted.

2. The variable stiffness catheter tubing of claim 1, further comprising a second extrusion segment placed over the inner layer of the multi-layer extrusion adjacent the first extrusion where the outer layer has been peeled away, the first and second extrusion segments joined together.

3. The variable stiffness catheter tubing of claim 2, wherein said second extrusion segment comprises a tungsten-filled polymer extrusion.

4. The variable stiffness catheter tubing of claim 1, wherein the inner layer of the multi-layer extrusion is formed of HDPE.

5. The variable stiffness catheter tubing of claim 1, wherein the inner layer of the multi-layer extrusion is formed of UHMWPE.

6. The variable stiffness catheter tubing of claim 1, wherein the outer layer of the multi-layer extrusion is formed of one of the group of nylon and Pebax.

7. The variable stiffness catheter tubing of claim 1, wherein an outer layer of the first extrusion segment and the outer layer of the multi-layer extrusion overlap.

8. The variable stiffness catheter tubing of claim 7, wherein the overlapping portions of the first extrusion segment and multi-layer extrusion are angle cut.

9. The variable stiffness catheter tubing of claim 1, wherein the catheter tubing is hot die necked.

10. The variable stiffness catheter tubing of claim 1, wherein the inner layer of the multi-layer extrusion is E-beam irradiated.

11. The variable stiffness catheter tubing of claim 1, wherein the first extrusion segment includes an inner tie layer to bond with the inner layer of the multi-layer extrusion.

12. The variable stiffness catheter tubing of claim 1, wherein the inner layer of the multi-layer extrusion is a fluoropolymer.

13. The variable stiffness catheter tubing of claim 12, wherein the inner layer is etched with sodium naphthalene.

* * * * *